(12) United States Patent
Liu et al.

(10) Patent No.: US 7,831,322 B2
(45) Date of Patent: Nov. 9, 2010

(54) PRODUCING WRINKLED DENTAL ALIGNER FOR DENTAL TREATMENT

(75) Inventors: Frank Zhenhuan Liu, Redwood City, CA (US); Huafeng Wen, Redwood City, CA (US)

(73) Assignee: Align Technology, Inc., Santa Clara, CA (US)

( * ) Notice: Subject to any disclaimer, the term of this patent is extended or adjusted under 35 U.S.C. 154(b) by 179 days.

(21) Appl. No.: 11/074,297

(22) Filed: Mar. 7, 2005

(65) Prior Publication Data

US 2006/0199153 A1  Sep. 7, 2006

(51) Int. Cl.
*G06F 19/00* (2006.01)
(52) U.S. Cl. .............................. 700/95; 433/24; 433/18; 433/213
(58) Field of Classification Search ......... 433/213–225, 433/6–21, 24; 700/95
See application file for complete search history.

(56) References Cited

U.S. PATENT DOCUMENTS

| | | |
|---|---|---|
| 4,755,139 A | 7/1988 | Abbatte |
| 4,798,534 A | 1/1989 | Breads |
| 4,856,991 A | 8/1989 | Breads |
| 4,936,862 A | 6/1990 | Walker |
| 5,011,405 A | 4/1991 | Lemchen |
| 5,035,613 A | 7/1991 | Breads |
| 5,055,039 A | 10/1991 | Abbatte |
| 5,059,118 A | 10/1991 | Breads |
| 5,186,623 A | 2/1993 | Breads |
| 5,273,429 A | 12/1993 | Rekow |
| 5,338,198 A | 8/1994 | Wu |
| 5,340,309 A | 8/1994 | Robertson |
| 5,342,202 A | 8/1994 | Deshayes |
| 5,368,478 A | 11/1994 | Andreiko |
| 5,382,164 A | 1/1995 | Stern |
| 5,452,219 A | 9/1995 | Dehoff |
| 5,478,235 A * | 12/1995 | Schuldt et al. ................ 433/37 |
| 5,549,476 A | 8/1996 | Stern |
| 5,587,912 A | 12/1996 | Andersson |
| 5,607,305 A | 3/1997 | Andersson |
| 5,645,421 A | 7/1997 | Slootsky |
| 5,879,158 A | 3/1999 | Doyle |
| 5,975,893 A | 11/1999 | Chishti |
| 6,217,325 B1 | 4/2001 | Chishti |
| 6,227,850 B1 | 5/2001 | Chishti |
| 6,227,851 B1 | 5/2001 | Chishti |
| 6,299,440 B1 | 10/2001 | Phan |
| 6,309,215 B1 | 10/2001 | Phan |
| 6,497,574 B1 | 12/2002 | Miller |
| 6,499,997 B2 | 12/2002 | Chishti |
| 6,514,074 B1 | 2/2003 | Chishti |
| 6,524,101 B1 | 2/2003 | Phan |
| 6,554,611 B2 | 4/2003 | Chishti |
| 6,572,372 B1 | 6/2003 | Phan |
| 6,582,227 B2 | 6/2003 | Phan |
| 6,582,229 B1 | 6/2003 | Miller |
| 6,602,070 B2 | 8/2003 | Miller |

(Continued)

*Primary Examiner*—Cris L Rodriguez
*Assistant Examiner*—Yogesh Patel
(74) *Attorney, Agent, or Firm*—Townsend and Townsend and Crew LLP

(57) ABSTRACT

A method for manufacturing wrinkled dental aligner for a patient's tooth includes developing a digital dental aligner model specifying at least one wrinkled surface on a dental aligner and producing a dental aligner having the wrinkled surface in accordance with digital dental aligner model.

19 Claims, 12 Drawing Sheets

U.S. PATENT DOCUMENTS

| | | |
|---|---|---|
| 6,607,382 B1 | 8/2003 | Kuo |
| 6,621,491 B1 | 9/2003 | Baumrind |
| 6,626,666 B2 | 9/2003 | Chishti |
| 6,629,840 B2 | 10/2003 | Chishti |
| 6,633,789 B1 | 10/2003 | Nikolskiy |
| 6,665,570 B2 | 12/2003 | Pavloskaia |
| 6,682,346 B2 | 1/2004 | Chishti |
| 6,685,469 B2 | 2/2004 | Chishti |
| 6,685,470 B2 | 2/2004 | Chishti |
| 6,688,886 B2 | 2/2004 | Hughes |
| 6,699,037 B2 | 3/2004 | Chishti |
| 6,705,861 B2 | 3/2004 | Chishti |
| 6,722,880 B2 | 4/2004 | Chishti |
| 6,726,478 B1 | 4/2004 | Isiderio |
| 6,729,876 B2 | 5/2004 | Chishti |
| 7,092,784 B1 * | 8/2006 | Simkins ............ 700/163 |
| 2002/0150855 A1 * | 10/2002 | Shishti et al. ............ 433/6 |
| 2003/0219690 A1 * | 11/2003 | Graham ............ 433/6 |
| 2005/0106525 A1 * | 5/2005 | Knopp et al. ............ 433/6 |
| 2006/0177789 A1 * | 8/2006 | O'Bryan ............ 433/6 |

* cited by examiner

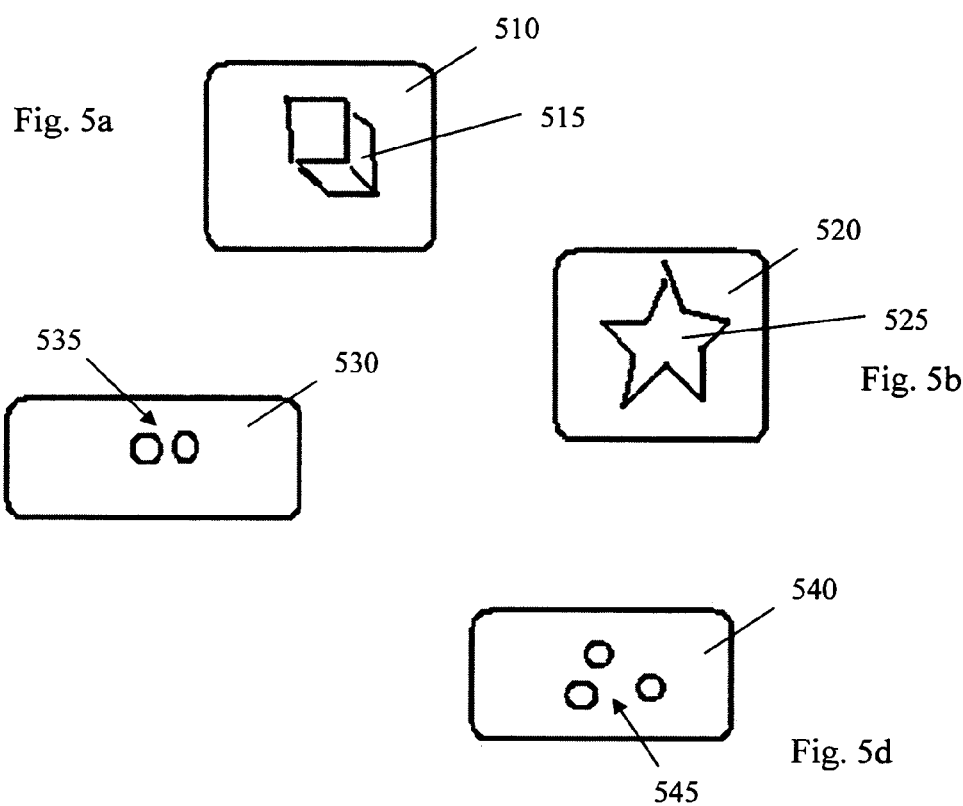

PRODUCING WRINKLED DENTAL ALIGNER FOR DENTAL TREATMENT

TECHNICAL FIELD

This application generally relates to the field of dental care, and more particularly to the field of orthodontics.

CROSS-REFERENCES TO RELATED INVENTIONS

The present invention is also related to concurrently filed and commonly assigned U.S. patent application titled "Producing physical dental arch model having individually adjustable tooth models" by Liu et al, U.S. patent application titled "Dental aligner for providing accurate dental treatment" by Liu et al, U.S. patent application titled "Fluid permeable dental aligner" by Huafeng Wen, and U.S. patent application titled "Disposal dental aligner" by Huafeng Wen.

The present invention is also related to commonly assigned U.S. patent application Ser. No. 10/979,823, titled "Method and apparatus for manufacturing and constructing a physical dental arch model" by Huafeng Wen, filed Nov. 2, 2004, U.S. patent application Ser. No. 10/979,497, titled "Method and apparatus for manufacturing and constructing a dental aligner" by Huafeng Wen, filed Nov. 2, 2004, U.S. patent application Ser. No. 10/979,504, titled "Producing an adjustable physical dental arch model" by Huafeng Wen, filed Nov. 2, 2004, and U.S. patent application Ser. No. 10/979,824, titled "Producing a base for physical dental arch model" by Huafeng Wen, filed Nov. 2, 2004. The disclosure of these related applications are incorporated herein by reference.

The present invention is also related to commonly assigned U.S. patent application Ser. No. 11/013,152, titled "A base for physical dental arch model" by Huafeng Wen, filed Dec. 14, 2004, commonly assigned U.S. patent application Ser. No. 11/012,924, titled "Accurately producing a base for physical dental arch model" by Huafeng Wen, filed Dec. 14, 2004, commonly assigned U.S. patent application Ser. No. 11/013,145, titled "Fabricating a base compatible with physical dental tooth models" by Huafeng Wen, filed Dec. 14, 2004, commonly assigned U.S. patent application Ser. No. 11/013,156, titled "Producing non-interfering tooth models on a base" by Huafeng Wen, filed Dec. 14, 2004, commonly assigned U.S. patent application Ser. No. 11/013,160, titled "System and methods for casting physical tooth model" by Huafeng Wen, filed Dec. 14, 2004, commonly assigned U.S. patent application Ser. No. 11/013,159, titled "Producing a base for accurately receiving dental tooth models" by Huafeng Wen, and filed Dec. 14, 2004, commonly assigned U.S. patent application Ser. No. 11/013,157, titled "Producing accurate base for dental arch model" by Huafeng Wen, filed Dec. 14, 2004. The disclosure of these related applications are incorporated herein by reference.

BACKGROUND

Orthodontics is the practice of manipulating a patient's teeth to provide better function and appearance. In general, brackets are bonded to a patient's teeth and coupled together with an arched wire. The combination of the brackets and wire provide a force on the teeth causing them to move. Once the teeth have moved to a desired location and are held in a place for a certain period of time, the body adapts bone and tissue to maintain the teeth in the desired location. To further assist in retaining the teeth in the desired location, a patient may be fitted with a retainer.

To achieve tooth movement, orthodontists utilize their expertise to first determine a three-dimensional mental image of the patient's physical orthodontic structure and a three-dimensional mental image of a desired physical orthodontic structure for the patient, which may be assisted through the use of x-rays and/or models. Based on these mental images, the orthodontist further relies on his/her expertise to place the brackets and/or bands on the teeth and to manually bend (i.e., shape) wire, such that a force is asserted on the teeth to reposition the teeth into the desired physical orthodontic structure. As the teeth move towards the desired location, the orthodontist makes continual judgments as to the progress of the treatment, the next step in the treatment (e.g., new bend in the wire, reposition or replace brackets, is head gear required, etc.), and the success of the previous step.

In general, the orthodontist makes manual adjustments to the wire and/or replaces or repositions brackets based on his or her expert opinion. Unfortunately, in the oral environment, it is impossible for a human being to accurately develop a visual three-dimensional image of an orthodontic structure due to the limitations of human sight and the physical structure of a human mouth. In addition, it is humanly impossible to accurately estimate three-dimensional wire bends (with an accuracy within a few degrees) and to manually apply such bends to a wire. Further, it is humanly impossible to determine an ideal bracket location to achieve the desired orthodontic structure based on the mental images. It is also extremely difficult to manually place brackets in what is estimated to be the ideal location. Accordingly, orthodontic treatment is an iterative process requiring multiple wire changes, with the process success and speed being very much dependent on the orthodontist's motor skills and diagnostic expertise. As a result of multiple wire changes, patient discomfort is increased as well as the cost. As one would expect, the quality of care varies greatly from orthodontist to orthodontist as does the time to treat a patient.

As described, the practice of orthodontic is very much an art, relying on the expert opinions and judgments of the orthodontist. In an effort to shift the practice of orthodontic from an art to a science, many innovations have been developed. For example, U.S. Pat. No. 5,518,397 issued to Andreiko, et. al. provides a method of forming an orthodontic brace. Such a method includes obtaining a model of the teeth of a patient's mouth and a prescription of desired positioning of such teeth. The contour of the teeth of the patient's mouth is determined, from the model. Calculations of the contour and the desired positioning of the patient's teeth are then made to determine the geometry (e.g., grooves or slots) to be provided. Custom brackets including a special geometry are then created for receiving an arch wire to form an orthodontic brace system. Such geometry is intended to provide for the disposition of the arched wire on the bracket in a progressive curvature in a horizontal plane and a substantially linear configuration in a vertical plane. The geometry of the brackets is altered, (e.g., by cutting grooves into the brackets at individual positions and angles and with particular depth) in accordance with such calculations of the bracket geometry. In such a system, the brackets are customized to provide three-dimensional movement of the teeth, once the wire, which has a two dimensional shape (i.e., linear shape in the vertical plane and curvature in the horizontal plane), is applied to the brackets.

Other innovations relating to bracket and bracket placements have also been patented. For example, such patent innovations are disclosed in U.S. Pat. No. 5,618,716 entitled "Orthodontic Bracket and Ligature" a method of ligating arch wires to brackets, U.S. Pat. No. 5,011,405 "Entitled Method for Determining Orthodontic Bracket Placement," U.S. Pat.

No. 5,395,238 entitled "Method of Forming Orthodontic Brace," and U.S. Pat. No. 5,533,895 entitled "Orthodontic Appliance and Group Standardize Brackets therefore and methods of making, assembling and using appliance to straighten teeth".

Kuroda et al. (1996) Am. J. Orthodontics 110:365-369 describes a method for laser scanning a plaster dental cast to produce a digital image of the cast. See also U.S. Pat. No. 5,605,459. U.S. Pat. Nos. 5,533,895; 5,474,448; 5,454,717; 5,447,432; 5,431,562; 5,395,238; 5,368,478; and 5,139,419, assigned to Ormco Corporation, describe methods for manipulating digital images of teeth for designing orthodontic appliances.

U.S. Pat. No. 5,011,405 describes a method for digitally imaging a tooth and determining optimum bracket positioning for orthodontic treatment. Laser scanning of a molded tooth to produce a three-dimensional model is described in U.S. Pat. No. 5,338,198. U.S. Pat. No. 5,452,219 describes a method for laser scanning a tooth model and milling a tooth mold. Digital computer manipulation of tooth contours is described in U.S. Pat. Nos. 5,607,305 and 5,587,912. Computerized digital imaging of the arch is described in U.S. Pat. Nos. 5,342,202 and 5,340,309.

Other patents of interest include U.S. Pat. Nos. 5,549,476; 5,382,164; 5,273,429; 4,936,862; 3,860,803; 3,660,900; 5,645,421; 5,055,039; 4,798,534; 4,856,991; 5,035,613; 5,059,118; 5,186,623; and 4,755,139.

The key to efficiency in treatment and maximum quality in results is a realistic simulation of the treatment process. Today's orthodontists have the possibility of taking plaster models of the upper and lower arch, cutting the model into single tooth models and sticking these tooth models into a wax bed, lining them up in the desired position, the so-called set-up. This approach allows for reaching a perfect occlusion without any guessing. The next step is to bond a bracket at every tooth model. This would tell the orthodontist the geometry of the wire to run through the bracket slots to receive exactly this result. The next step involves the transfer of the bracket position to the original malocclusion model. To make sure that the brackets will be bonded at exactly this position at the real patient's teeth, small templates for every tooth would have to be fabricated that fit over the bracket and a relevant part of the tooth and allow for reliable placement of the bracket on the patient's teeth. To increase efficiency of the bonding process, another option would be to place each single bracket onto a model of the malocclusion and then fabricate one single transfer tray per arch that covers all brackets and relevant portions of every tooth. Using such a transfer tray guarantees a very quick and yet precise bonding using indirect bonding.

U.S. Pat. No. 5,431,562 to Andreiko et al. describes a computerized, appliance-driven approach to orthodontics. In this method, first certain shape information of teeth is acquired. A uniplanar target arcform is calculated from the shape information. The shape of customized bracket slots, the bracket base, and the shape of the orthodontic archwire, are calculated in accordance with a mathematically-derived target archform. The goal of the Andreiko et al. method is to give more predictability, standardization, and certainty to orthodontics by replacing the human element in orthodontic appliance design with a deterministic, mathematical computation of a target archform and appliance design. Hence the '562 patent teaches away from an interactive, computer-based system in which the orthodontist remains fully involved in patient diagnosis, appliance design, and treatment planning and monitoring.

More recently, Align Technology, Inc. began offering transparent, removable aligning devices as a new treatment modality in orthodontics. In this system, an impression model of the dentition of the patient is obtained by the orthodontist and shipped to a remote appliance manufacturing center, where it is scanned with a CT scanner. A computer model of the dentition in a target situation is generated at the appliance manufacturing center and made available for viewing to the orthodontist over the Internet. The orthodontist indicates changes they wish to make to individual tooth positions. A revised virtual model is provided for the orthodontist to review, until the target situation is agreed upon. A series of removable aligning devices or shells are manufactured and delivered to the orthodontist. The shells will move the patient's teeth to the desired or target position.

U.S. Pat. No. 6,699,037 describes improved methods and systems for repositioning teeth from an initial tooth arrangement to a final tooth arrangement. Repositioning is accomplished with a system comprising a series of appliances configured to receive the teeth in a cavity and incrementally reposition individual teeth in a series of successive steps, usually including at least four successive steps, often including at least ten steps, sometimes including at least twenty-five steps, and occasionally including forty or more steps. Most often, the methods and systems will reposition teeth in from ten to twenty-five successive steps, although complex cases involving many of the patient's teeth may take forty or more steps. The successive use of a number of such appliances permits each appliance to be configured to move individual teeth in small increments, typically less than 2 mm, preferably less than 1 mm, and more preferably less than 0.5 mm. These values refer to the maximum linear translation of any point on a tooth as a result of using a single appliance. The movements provided by successive appliances, of course, will usually not be the same for any particular tooth. Thus, one point on a tooth may be moved by a different distance as a result of the use of one appliance and thereafter moved by a different distance and/or in a different direction by a later appliance.

The individual appliances preferably comprise a polymeric shell having the teeth-receiving cavity formed therein, typically by molding. Each individual appliance is configured so that its tooth-receiving cavity has a geometry corresponding to an intermediate or end tooth arrangement intended for that appliance. That is, when an appliance is first worn by the patient, certain of the teeth will be misaligned relative to an undeformed geometry of the appliance cavity. The appliance, however, is sufficiently resilient to accommodate or conform to the misaligned teeth, and will apply sufficient resilient force against such misaligned teeth in order to reposition the teeth to the intermediate or end arrangement desired for that treatment step.

The fabrication of aligners utilizes using a stereo lithography process as is disclosed in U.S. Pat. Nos. 6,471,511 and 6,682,346. The stereo lithography process builds the aligner layer by layer, and may use a different aligner mold at each stage of the treatment. There is therefore a long felt need for practical, effective and efficient methods to produce a dental aligner.

Another long recognized issue with the dental aligners is that an aligner often becomes relaxed and open up after repeated usage by a patient, which causes a loss of corrective forces applied by the aligner to the patient's teeth. This results in insufficient or inaccurate teeth movement and costly corrective measures in the orthodontic treatment.

SUMMARY OF THE INVENTION

The present invention has been devised to substantially eliminate the foregoing problems and is to provide methods and apparatus to manufacture and construct the physical dental arch model. Implementations of the system may include one or more of the following.

In one aspect, the present invention relates to a method for manufacturing wrinkled dental aligner for a patient's tooth, comprising:

developing a digital dental aligner model specifying at least one wrinkled surface on a dental aligner; and producing a dental aligner having the wrinkled surface in accordance with digital dental aligner model.

In another aspect, the present invention relates to a method for manufacturing wrinkled dental aligner for a patient's arch, comprising:

developing a digital dental arch model based the patient's arch;

developing a digital dental aligner model based on the digital dental arch model, wherein the digital dental aligner model specifies one or more wrinkles on a surface; and producing a wrinkled dental aligner in accordance with the digital dental aligner model.

In yet another aspect, the present invention relates to a system for manufacturing a wrinkled dental aligner for a patient, comprising:

a computer configured to store a digital dental aligner model specifying at least one wrinkled surface on the wrinkled dental aligner; and an apparatus configured to produce the wrinkled dental aligner in accordance with digital dental aligner model.

Embodiments may include one or more of the following advantages. The present invention provides practical methods and system for making a wrinkled dental aligner. The wrinkled aligner prevents the relaxation of the dental aligner after repeated uses, which is common in prior art systems. The wrinkled dental aligner therefore can ensure the aligner to produce the correct force to produce desirable movement in the patient's teeth, which improves the accuracy and effectiveness of the orthodontic treatment by the aligner.

The reduction or elimination of the relaxation and force loss that are problems associated with the conventional dental aligners also have the benefit of lengthening the lifetime of the aligner. As a result, the number of visits to the dentist office is reduced. The material and manufacture costs of the aligners for an orthodontic treatment are decreased. An additional advantage is that the probability for corrective rework due to aligner deformation is significantly reduced, which further reduces costs of the orthodontic treatment.

A further advantage of the present invention is that the properties of the wrinkled aligners can be simulated and optimized in the design process. The performance of the wrinkled aligners can be optimized by simulating and varying wrinkle parameters such as wrinkle depth, wrinkle location and orientation, and wrinkle density. The wrinkled dental aligner can be manufactured by cost-effective processes such as vacuum forming, cutting by a cutter, etching by a laser beam or thermal applier, or CNC based manufacturing.

The details of one or more embodiments are set forth in the accompanying drawing and in the description below. Other features, objects, and advantages of the invention will become apparent from the description and drawings, and from the claims.

BRIEF DESCRIPTION OF THE DRAWINGS

The accompanying drawing, which are incorporated in and form a part of this specification, illustrate embodiments of the invention and, together with the description, serve to explain the principles of the invention:

FIGS. 5a-d illustrates aligner components comprising features that allow them to assembled to form an aligner.

DETAILED DESCRIPTION OF EMBODIMENTS

Figure 1:
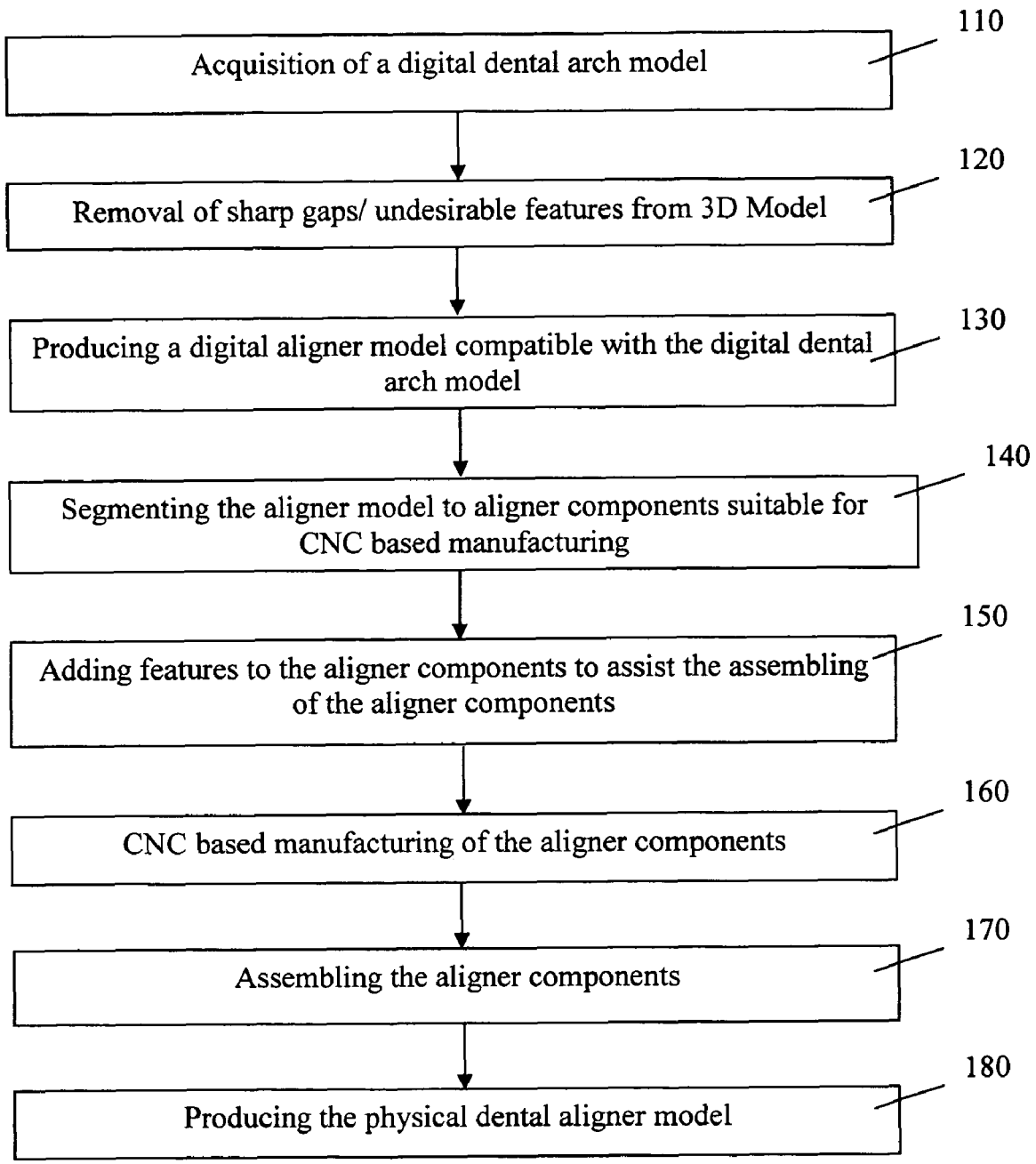
FIG. 1 is a flow chart for producing a physical aligner in accordance with the present invention.

FIG. 1 illustrates the process of producing a dental aligner in accordance with the present invention. In the present application, the term "dental aligner" refers to a dental device for correcting malocclusion. First, a three dimensional (3D) digital dental arch model is acquired from a patient's arch in step 110. The digital dental arch model can be obtained by 3D scanning of a cast produced from the patient's arch. The digital model includes a mesh of points in three dimensions that define the surfaces of an entire or a large portion of an upper or lower arch. Details of obtaining a digital model of an arch are disclosed in above referenced U.S. patent application titled "Producing a base for a physical dental arch model" by Huafeng Wen, filed Dec. 14, 2004, the content of which is incorporated herein by reference.

Next, in step 120, the digital dental arch model is smoothened by computer processing using a computer software. One or more criteria for the degree of smoothness can also be provided by a user. Undesirable features such as sharp gas and divots are removed from the digital dental arch model.

The criteria for the degree of smoothness can be required by the specific dental applications. The plastic aligners for example cannot reach into the gaps between the teeth. In addition, it is also undesirable to have aligner to have fine features inside the gaps because that could potentially create resistance to desired tooth movement in a orthodontics treatment procedure.

The criteria for the degree of smoothness can also be required by type of the tools used to manufacture the aligner components as described below. In the present invention, Computer Numerical Control or CNC based manufacturing refers to the automated and computer controlled machining. The most basic function of a CNC machine is automatic, precise, and consistent motion control. All forms of CNC equipment have two or more directions of motion, called axes. These axes can be precisely and automatically positioned along their lengths of travel. The two most common axis types are linear (driven along a straight path) and rotary (driven along a circular path). Instead of causing motion by manually turning cranks and hand wheels as is required on conventional machine tools, CNC machines allow motions to be actuated by servomotors under control of the CNC, and guided by the part program. Generally speaking, the motion type (rapid, linear, and circular), the axes to move, the amount of motion and the motion rate (feed rate) are programmable with almost all CNC machine tools. In the present invention, in addition to CNC based milling, the CNC based manufacturing is also compatible with other computer numerical controlled manufacturing processes such as stereolithography, laser machining, molding as well as other types of CNC based machining.

For manufacturing a physical dental arch model, however, the drill bit in CNC based milling is usually too big to reach into the gaps and holes in a dental arch model. CNC milling is usually around one axis, which makes it difficult to machine the complex shapes within the gaps between teeth. CNC based milling also has limitations in accuracy and repeatability between different stages of milling.

Several techniques have been used to remove the gaps in the digital dental arch model to produce a smoothened digital dental arch model:

1. Boolean union with primitive 3D objects. Graphics Constructive Solid Geometry primitives or self developed predefined geometries can be inserted into the gaps in the digital dental arch model and then combine with the original 3D digital mesh.
2. Extrusion. The surfaces near the gaps are extruded to fill the gaps in the original 3D digital mesh.
3. Geometry modification by moving vertices. Sharp gaps can be closed by specifying the desired boundaries and modifying the mesh to the desired boundaries in the problem regions.
4. Subdivision of surfaces and movement. Similar to Technique 3, the dental arch surfaces are subdivided in the regions of surface modification for greater smoothness and continuity.
5. Convex hull creation of sub parts to be used as filling objects in the gaps. The gap regions are first located and the points defining edges of the sharp gaps are identified. A convex hull is computed based on these points. The convex hull is joined with the original mesh to fill the gaps using Boolean union.
6. Using parametric surfaces to model fill objects that will be used fit in the gaps.

Figure 2:
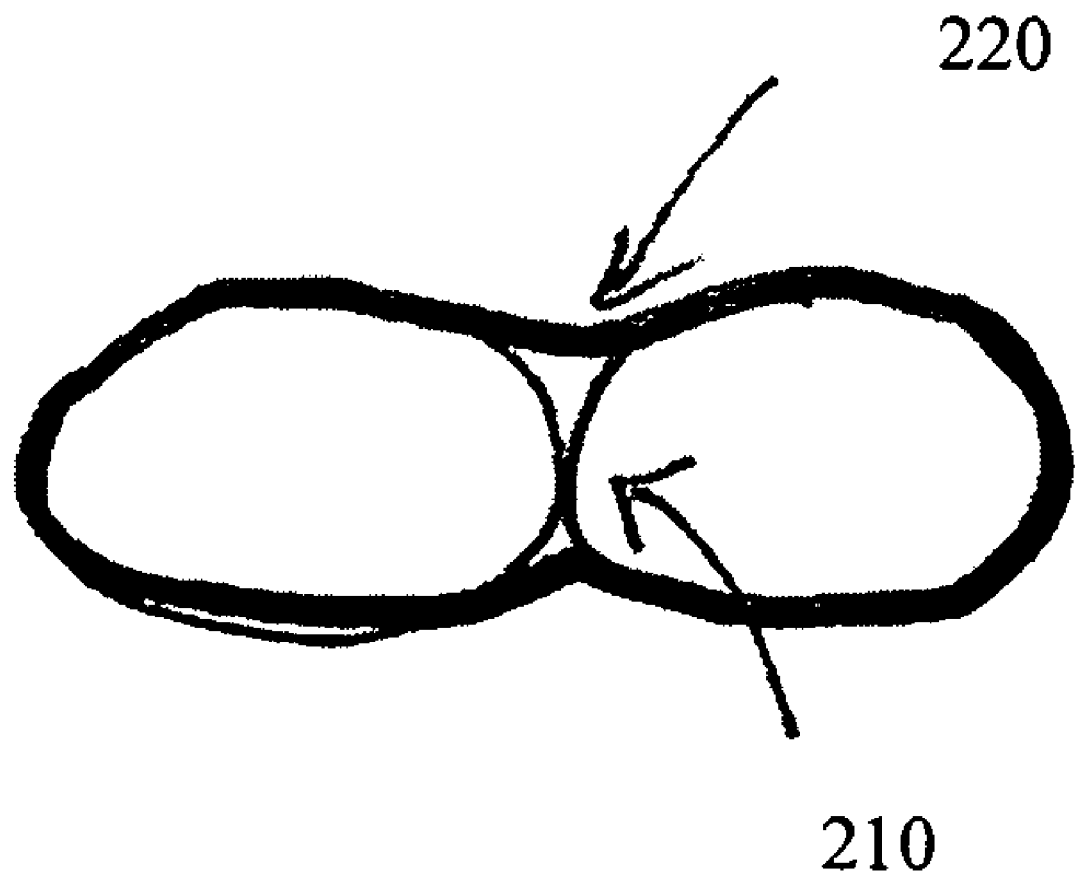
FIG. 2 illustrates the smoothening of the digital aligner model in preparation for a CNC based manufacturing of physical aligner in accordance with the present invention.

FIG. 2 illustrates the smoothening effects of the gap filling by comparing the surfaces 210 of before gap fillings and the surfaces 220 after the gap fillings.

A simulation can be conducted using the smoothened the digital dental arch model as input to check and verify the smoothness of the digital dental arch model. The simulation can be run using a simulator software in response to the smoothness criteria required by the manufacturing process such as CNC based milling or the dental applications. Refinement ad smoothening iterations may be called for if the smoothness criteria are not completely satisfied.

A digital aligner model is next developed based on the digital dental arch model in Step 130. The digital aligner model comprises inner surfaces and outer surfaces. Since the inner surfaces of the aligner will be in contact with the outer surface of the patient's teeth, the inner surfaces of the digital aligner model approximately follow the contours of the outer surface of the digital dental arch model, so that the dental aligner will snap on the arch. Moreover, the inner and outer surfaces of digital aligner are designed to various shapes and thickness to apply the right forces to achieve the movement of the teeth in accordance with a treatment plan.

Figure 3:
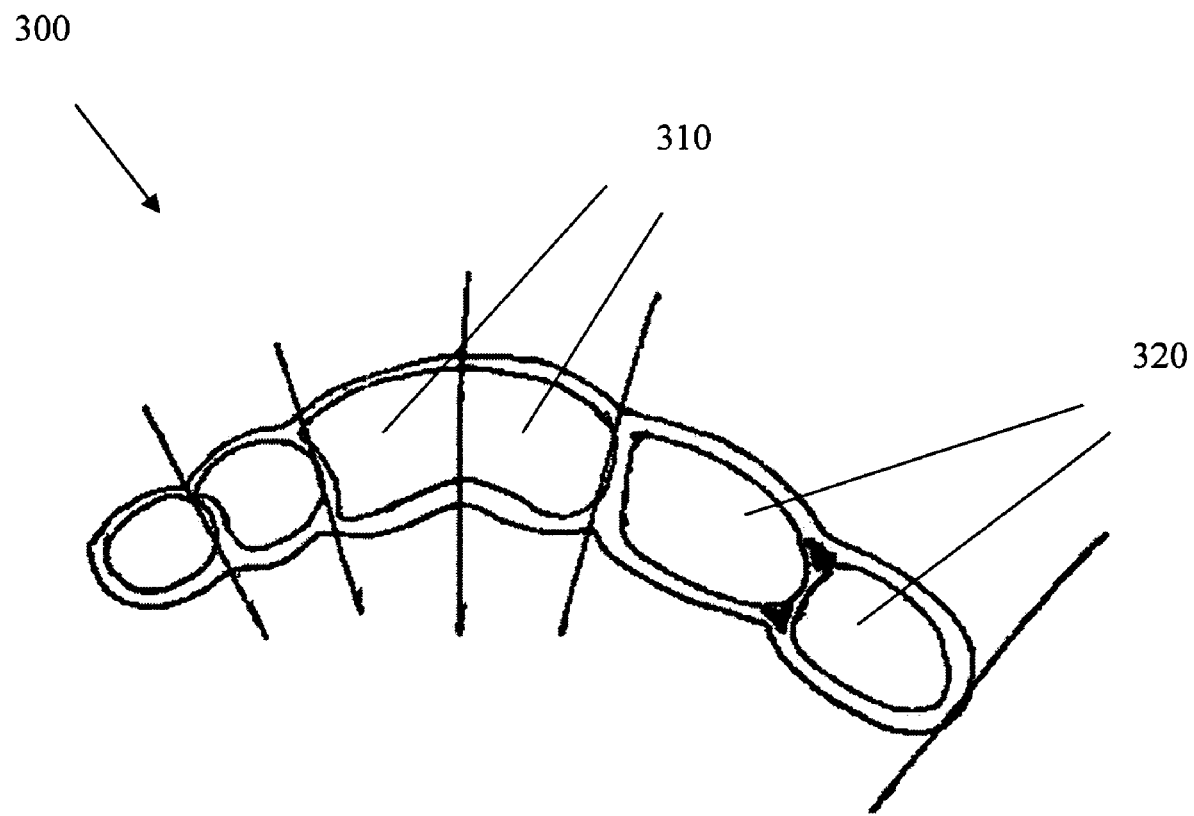
FIG. 3 illustrates the segmentation of digital aligner model into segmented components suitable for CNC based manufacturing in accordance with the present invention.

Next, in Step 140, the digital aligner model are segmented into digital aligner components suitable for CNC manufacturing. A typical aligner in the digital aligner model includes an upper or lower aligner respectively for the upper and lower arch or a portion of an arch comprising a plurality of teeth. An aligner 300 is shown in FIG. 3. The aligner components 310,320 can correspond to a portion of a tooth, a whole individual tooth, or sometimes a segment of arch including several teeth.

The criteria for the size, location, and the number of aligner components are based on both orthodontic needs and manufacturing requirements. The orthodontic criteria require the tracking of how the original locations of the aligner components and which components can be moved together as a group, which aligner components must be moved independently, and which teeth cannot be moved.

The manufacturing requirements relate mainly to the manufacturability of the digital aligner components, which usually supersedes the orthodontic criteria. For example, a single tooth can be divided into multiple components to make its model manufacturable. The segmented digital components can be evaluated by a simulation software to verify their manufacturability by a specific manufacture process such as CNC based milling, which may suggest refinement in the size, location, and numbers of the segmentation. The simulation can also include an evaluation and estimation of the physical strength after the assembly, as described below, to determine if the assembled aligner components are strong enough to withstand the physical forces in a pressure forming process.

In one embodiment, the digital aligner model can be smoothened during the segmentation. Different segmented digital components may receive different types or degree of smoothening so that the smoothening is tailored to the segments and manufacturing requirements.

An advantage of the present invention is that an aligner model is segmented to small manufacturable aligner components that can be manufactured by automated, precise numerical manufacturing techniques.

A further advantageous feature of the present invention is that the manufacturability of the digital components are simulated, verified and refined if necessary prior to manufacturing. As a result, complex aligner shapes that cannot be made can now be practically manufactured. Waste and cycle times are reduced in the process from design, testing, pilot, to production.

In step 150, features are added to the aligner components to assist the assembling of the aligner components to form an aligner. The features may include a pin, a registration slot, a notch, a protrusion, a hole, an interlocking mechanism, a socket, a jig, and a pluggable or an attachable feature. The adjacent manufactured aligner components may include matching male (e.g. mushroom, push pins) and female features (e.g. hole, notches etc.) for attachment. The male and female features can be fabricated for example by casting mold that include female and male matching features in the mold, each responsible for making respective male and female features. The adjacent aligner components can attached together by simply pushing male feature into the female feature, for example, by pressing a pushpin into a receiving hole.

Figure 4A:
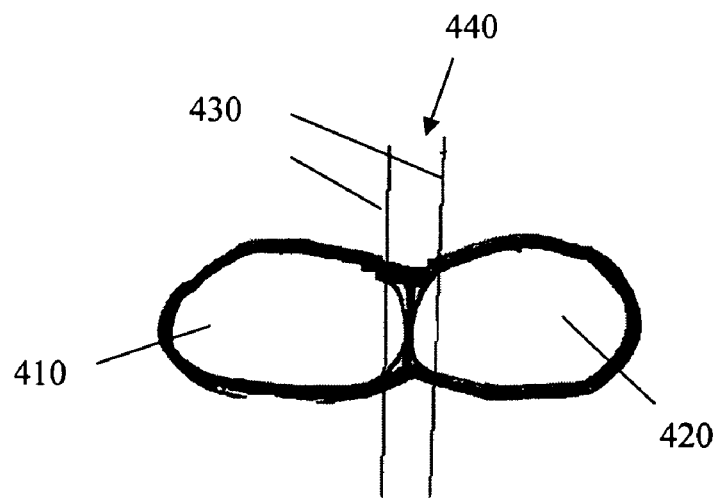
FIGS. 4a-4d illustrate the segmentation of an inter-proximal region by removing a space around the inter-proximal region and replacing it by a wedge.
Figure 4B:
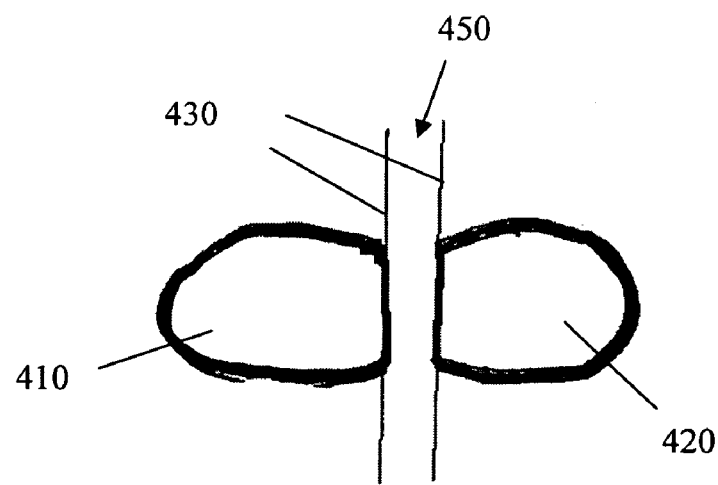

In another embodiment, special care needs to be applied to the inter-proximal regions in segmenting arch into digital components. In many cases, the inter-proximal regions involve such complexity and details that CNC based manufacturing such as cutting or milling cutting can result in losing details. As shown in FIGS. 4a and 4b, an inter-proximal region 440 is removed between a tooth model 410 and a tooth model 420 along the lines 430. This can be achieved by data processing over the digital dental arch model. A thin gap 450 is formed between tooth model 410 and tooth model 420.

Figure 4C:
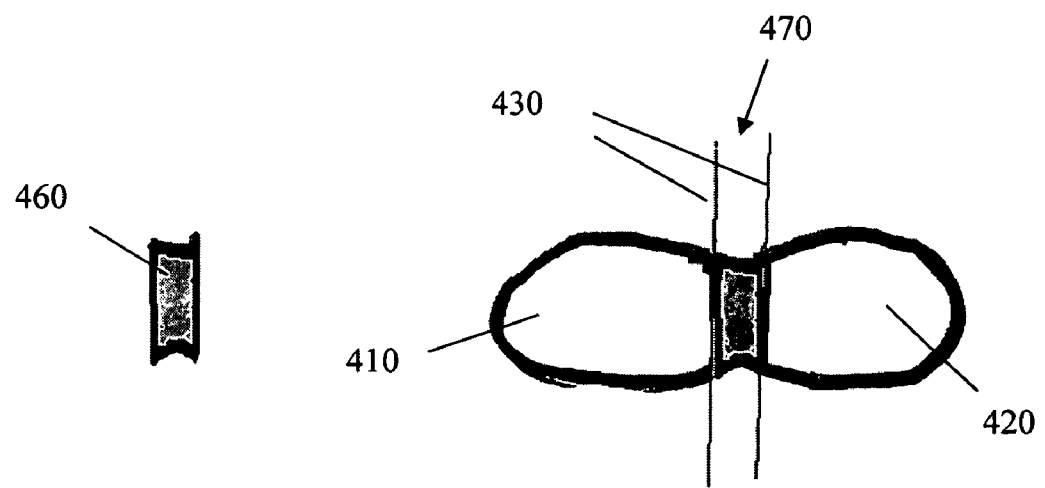
Figure 4D:
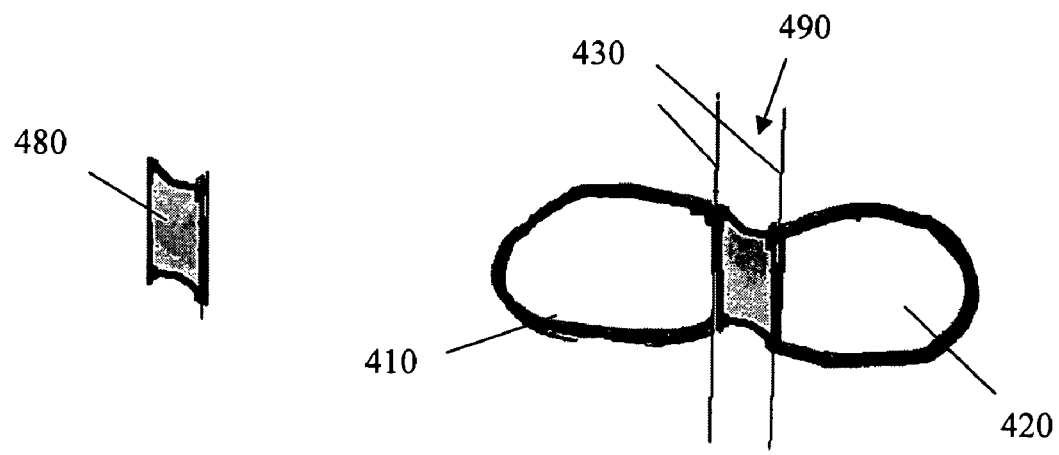

A wedge 460, shown in FIG. 4c, is then made using CNC based manufacturing technique similar to other manufacturable digital components. The wedge 470 can be inserted into the gap 450 to complete the digital tooth arch model. The wedge making and insertion can take into account of the movement of the tooth models 410, 420 during the orthodontic treatment. As shown FIG. 4d, the wedge 480 is made to be slightly sheared. The wedge 490 inserted between the tooth models 410, 420 can therefore induce a relative movement between the tooth models 410, 420. In general the relative movement can include translational and directional adjustment in different degrees of freedoms. The resulted tooth arch model can then be used to made dental aligners.

FIGS. 5a, 5b, 5c and 5d illustrate examples of the features in the aligner components 510,520,530,540. The features 515,525,535,545 allow the aligner components 510,520,530, 540 to be attached to each other to form a whole or part of a physical aligner. FIG. 5a shows a feature 515 having a cubic base for a aligner component 510. FIG. 5b shows a feature 525 having a star-shaped base for a aligner component 520. The star-shaped base defines unique orientation when aligner component 520 is assembled with another aligner component. FIGS. 5c and 5d show features 535 and 545 respectively comprising two and three pins in the aligner components 530 and 540. The two pins ensure uniquely defined orientation when aligner component 530 is assembled with another aligner component. Similarly, the three pins in feature 545 ensure unique configuration when aligner component 540 is assembled with another aligner component.

The aligner components 310,320 are manufactured in Step 160 using CNC based manufacturing techniques. The segmented digital aligner components are provided to as CNC objects input to a CNC machine. The aligner components 310,320 are manufactured individually. In the disclosed methods and systems, the precision and yield of the CNC based manufacturing are high because manufacturability has been considered and verified as part of the designs of the aligner components. Common materials for the aligner components include polymers, urethane, epoxy, plastics, plaster, stone, clay, acrylic, metals, wood, paper, ceramics, and porcelain. A mechanism may be required to hold the components in place during the milling process.

As described in more detail below, the digital dental aligner model can include wrinkle features to be produced on the aligner components and finally formed on the surfaces of the physical dental aligner. The wrinkle features can be pre-designed and simulated to reduce the relaxation of the aligner after repeated use. The wrinkled aligner or aligner components can be fabricated in accordance with the digital dental aligner model.

Figure 6:
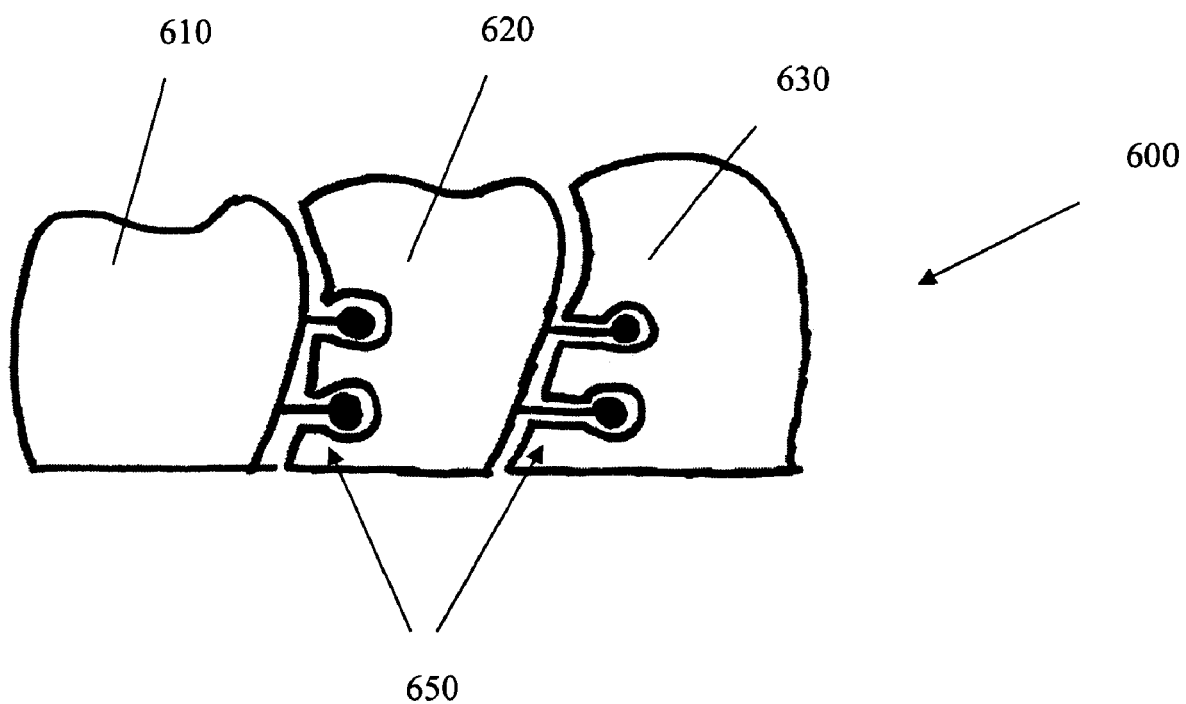
FIG. 6 illustrates an aligner assembled from a plurality of aligner components each comprising features that assist the assembling.

The physical aligner model 600 is assembled in Step 170 by assembling the aligner components. FIG. 6 illustrates how the aligner components 610, 620, 630 can be assembled to form a whole or a portion of a physical aligner model 600. The different aligner components 610,620,630 can be attached or plugged into each other at joining features 650 that can be pins, registration slot, a notch, etc.

The physical aligners can be used in different dental applications such as dental crown, dental bridge, dental retainer, mouth guard and teeth whitening. For aligner fabrication, for example, each stage of the teeth treatment may correspond a unique physical aligner model. Aligners can be fabricated based on the digital dental arch model as the teeth movement progresses during the treatment. At each stage of the treatment, the desirable teeth positions for the next stage are calculated. A physical aligner model is fabricated using the process described above for modifying teeth positions in Step 180.

In one aspect, the disclosed methods and system allow variable shape and thickness in the aligner designs comparing the prior art systems. Moreover, the disclosed methods and system provides wider range of aligner material selections. Analyses over aligner shape can be conducted done to ensure the optimal shape of aligner to be produced to achieve the desired movements at each stage of the orthodontic treatment. In addition, aligners having optimized shapes can achieve certain movements that the prior art cannot achieve. The aligners can be made thinner and more cosmetic, allowing more comfort in wearing. The manufacturing process is more consistent and easy.

The aligner components can be labeled with unique identifications, and assembled and detached in predetermined sequences. The assembling and detachment can be automated by for example a robotic arm under the control of a computer in accordance with the predetermined sequences.

In one embodiment, the aligner components are assembled in pressure forming. The aligner components may be hollow inside and have outer surfaces that match the digital aligner components to allow proper union of the aligner components. In another embodiment, the aligner components can be pre-fabricated similar to LEGO blocks. The surfaces of the aligner components may include standard registration and attaching features for them to join together. The LEGO-like aligner components can be assembled automatically by robotic arms under computer control. The aligner components can be separated and repaired after the assembly. The attaching features between aligner components allow the components to be detached in a sequence. Broken component can be removed, repaired or replaced, followed by re-assembling.

In another aspect of the present invention, system and methods are provided to overcome a long recognized issue with the dental aligners. The aligners are made of plastic materials and can often become relaxed and open up after repeated usage by a patient. The patient can bite the aligner to cause aligner to bend outwards. Each time the patient takes off the aligner during eating, drinking, or before sleep, the bottom part of the aligner tend to open up and relax. Furthermore, the material relaxation at bottom of the aligner over usage time can render ineffective application of force at the bottom of the teeth. The relaxation of the aligner can occur in as short a period as a few days of usage. The loss of corrective force applied by the aligner to the patient's teeth results in insufficient or inaccurate teeth movement. The corrective measures can include reordering of the same aligners and delay in the orthodontic treatment, which are costly for the patients.

Figure 7A:
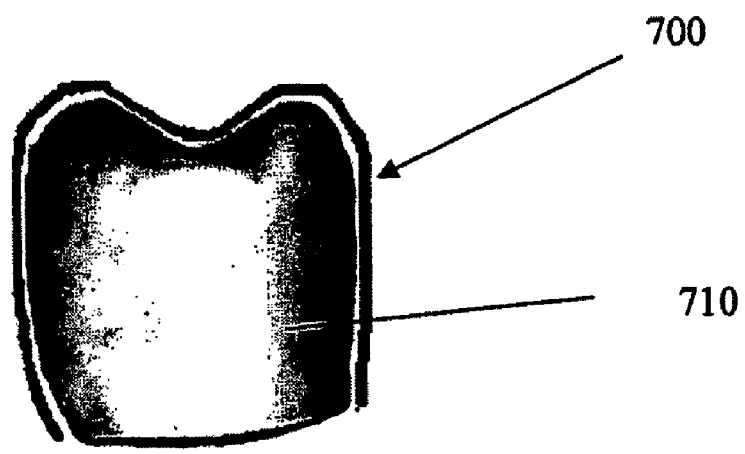
FIG. 7a illustrates the side view of a new conventional dental aligner worn a patient's tooth.
Figure 7B:
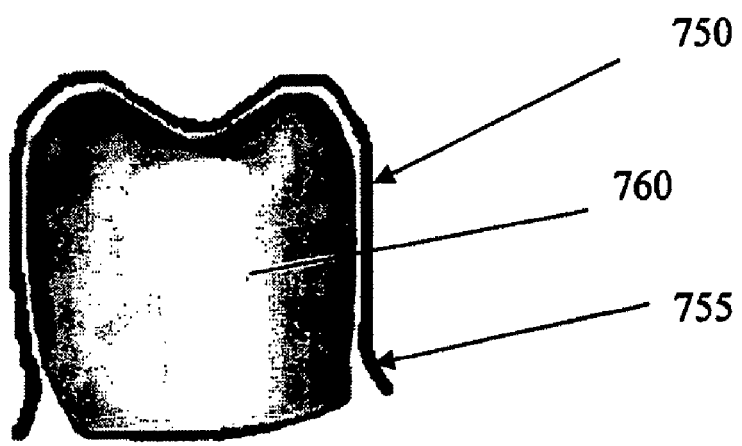
FIG. 7b shows the side view of a conventional dental aligner worn after a period of usage.
Figure 8:
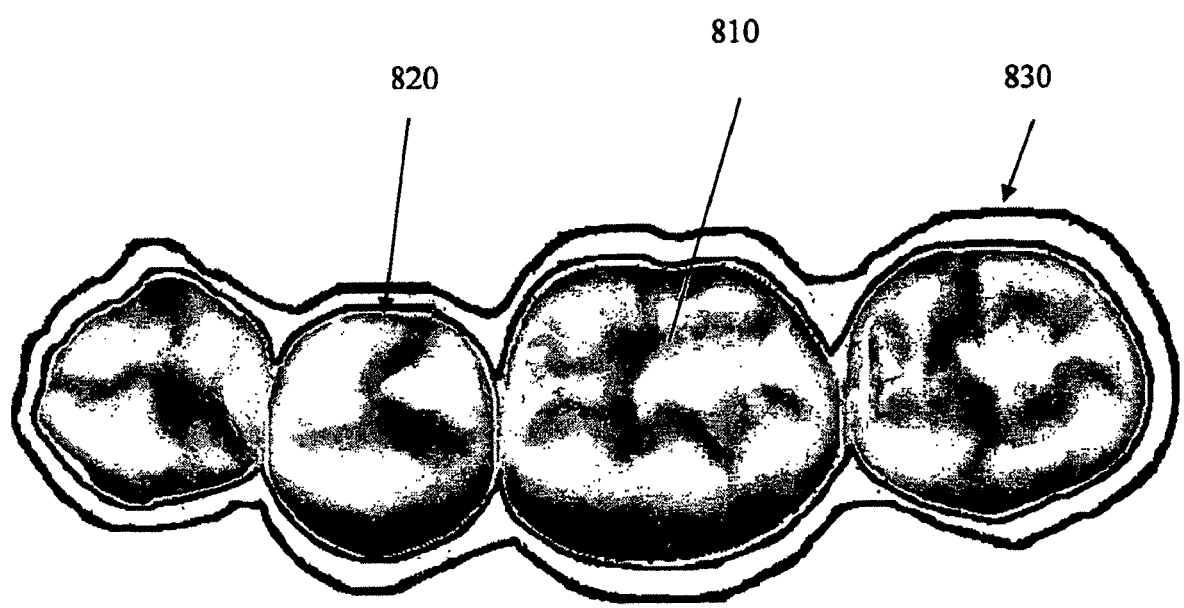
FIG. 8 illustrates the top views of a conventional dental aligner when it is newly worn and after it is worn for a period of time.

To illustrate the above described problem, FIG. 7a illustrates a side view of a new aligner 700 worn a patient's tooth 710. The aligner is typically in a shell shape, comprising shell portion, a tip portion, and a bottom portion. The inner surface of the shell portion is to be in contact with the patient's teeth. The aligner fits properly at the bottom of the tooth where the gingival separates the tooth from the root. The newly worn aligner 700 provides proper and effective force for the tooth movement in the orthodontic treatment. FIG. 7b shows the side view of the aligner 750 that has been worn on the patient's tooth 760 after a period of usage such as a few days or a week. The lower part 755 of the dental aligner 750 is relaxed and opened up, which prevents the dental aligner 750 to exert proper stress on the bottom of the tooth. The dental aligner 750 thus can no longer produce effective and accurate tooth movement. FIG. 8 illustrates the top view of a conventional dental aligner 820 that is newly worn on a patient's tooth 810. After it is worn for a period of time, the dental aligner 830 is relaxed and loose. It can no longer apply effective forces to the tooth 810.

Figure 9:
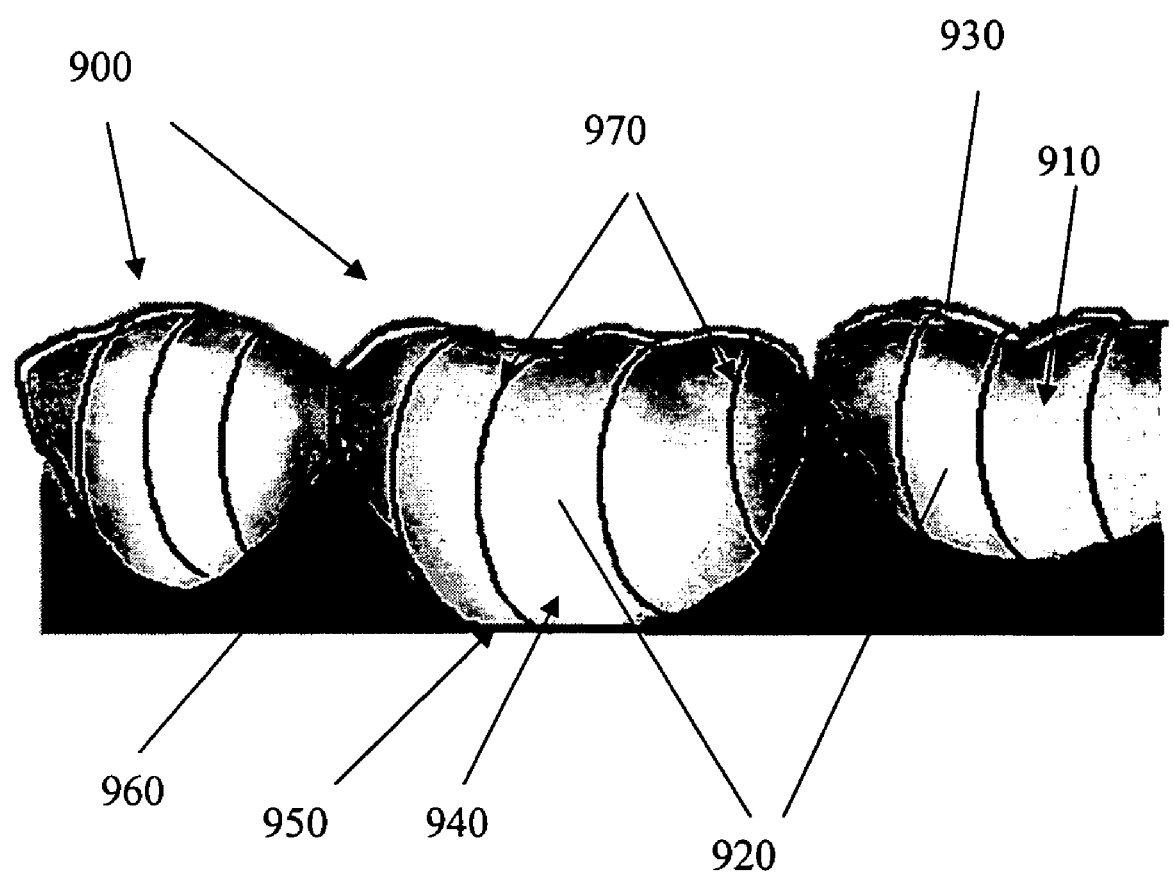
FIG. 9 illustrates an arrangement of the wrinkles on aligners.

In accordance with the present invention, wrinkle shaped aligner are designed and fabricated to overcome the loss of force caused by the relaxation of the aligners. Wrinkled aligners can include different designs. As shown in FIG. 9, a wrinkled aligner 900 can include a shell portion 910 that has an inner surface to be in contact with the patient's teeth, an outer surface 920, a tip portion 930, a bottom portion 940 along the base line 950 of the shell portion 910. The shell portion 910 can have varying thicknesses in different areas. The shell portion 910 can also comprise a plurality of layers of the same or different materials.

The dental aligner 900 is worn over the patient teeth over gum 960. Wrinkles 970 can be produced on one of or both the outer surface 920 (i.e. the buccal side) and the inner surface (i.e. lingual side) of the wrinkled aligner 900. The wrinkles 970 can be aligned from tip portion 930 to the bottom portion 940 of the wrinkled aligner 900 at a predetermined spacing between the adjacent wrinkles. The wrinkles 970 allow the wrinkled aligner 900 to relax when it receives stresses during patient's biting, or when the aligner is taken off and put on. The wrinkled shape can automatically restore when the stresses are removed. The wrinkled aligner 900 therefore is free of the relaxation problems in the prior art aligners. In other words, the wrinkled aligners 900 include robust structure designs that can tolerate stresses and maintain functional shape under stresses.

The wrinkles can be formed in different orientations and locations of the shell-shaped dental aligners. The wrinkle can also be made in parallel to the base line 950 of the wrinkled aligner 900 (i.e. across the direction from the tip portion 930 to the bottom portion 940), which helps to prevent the wrinkled aligner to open near the base. The wrinkles can also be produced in both horizontal (parallel to the base line 950 of the aligner) and vertical (from the tip portion to the bottom portion) directions. In another arrangement, a corrugated structure or "wrinkles" can be produced along the on the base line 950 of the wrinkled aligner 900. The corrugated structure along the base line 950 can generate elastic shrinking stress over the tooth, which can overcome the above described relaxation problem and extends the life of the wrinkled aligner 900. Various wrinkle arrangements can be applied singularly or in combination for optimize performance.

Wrinkled aligners can be fabricated by a variety of manufacturing methods. In one arrangement of aligner manufacturing, a patient's dental arch model is placed on a base plate of a vacuum former machine. The digital dental aligner model specifies a shell portion including an outer surface and an inner surface to be in contact with the patient's tooth, a bottom portion to be placed near the gingival of the patient's tooth, and a tip portion on the opposite side of the bottom portion. The digital dental aligner model also defines one or more wrinkles formed over at least one of the outer surface of the shell portion, the inner surface of the shell portion, and the bottom portion. An apparatus produces a physical dental aligner having a wrinkled surface in accordance with the digital dental aligner model.

Figure 10:
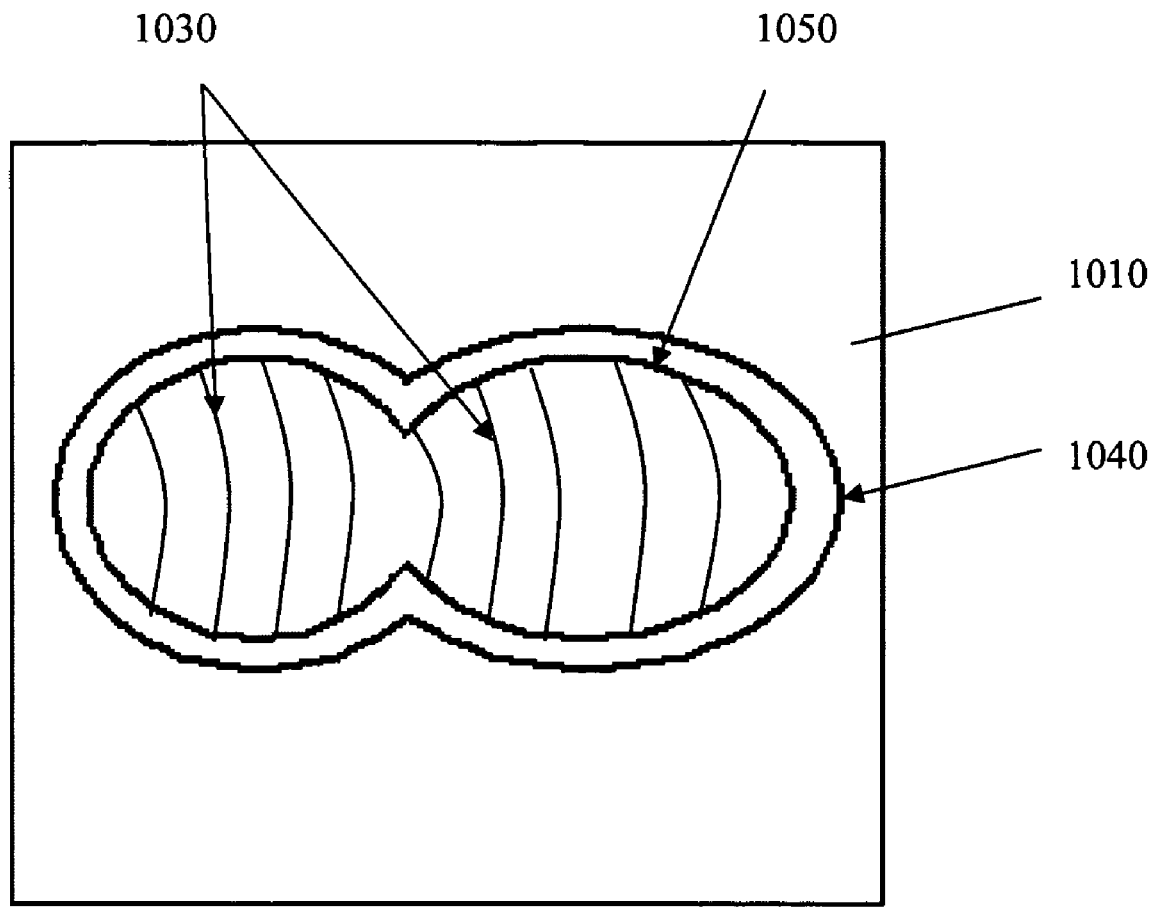
FIG. 10 illustrates the fabrication of a wrinkled aligner from a sheet of aligner material.

As shown in FIG. 10, a sheet 1010 of aligner-making material is attached to a sheet holder and then lifted up near a heating element. The sheet can be made of uniform distribution of a single material or comprise multiple layers of different materials. After the aligner-making material is heated by a specified time, the sheet holder is pressed on the patient's dental arch model on the base plate. A vacuum pump removes air at the bottom of the base plate to cause the softened aligner making material to relax and fittingly form around the surface the patient's dental arch model. The sheet of the aligner making material is then cut out along the gingival line 1040 to produce an aligner 1050 that can perfectly fit to the patient teeth. This process of aligner making is referred to as the vacuum forming.

In one method of wrinkle making, some material is extruded on other tooth surfaces of the patient's dental arch model that is fixed on to the base plate. The protrusions formed by the extruded material are distributed (e.g. the locations and the density of the wrinkles, the width and the depth of the wrinkles, etc.) to compatible with the wrinkles to be formed over the aligner. The extruded material is subsequently hardened over the surfaces of the arch model. When the soft sheet of aligner making material is pressed over the arch model, the protrusions formed by the extruded material produce the wrinkles 1030 on the sheet of the aligner making material. A wrinkled aligner 1050 is obtained after the cutting of the sheet.

In a variation of the above method of manufacturing wrinkled aligners, a high-tension material is placed at the locations of the dental arch model where the wrinkles are to be formed. The high strength material is absorbed and become embedded into the aligner material after the sheet of aligner making material is heated and pressed over the arch model. The distribution of high strength material creates an uneven elasticity distribution over the aligner surface that produces the wrinkles 1030.

In yet another embodiment, a high-tension material is placed in parallel stripes over the sheet of aligner making material before it is placed in the sheet holder. The subsequent heating causes the high-tension material to penetrate and embed in the sheet, which produces wrinkles 1030 in the wrinkled aligner 1050.

In another embodiment, a physical dental aligner without wrinkles is first produced by the above described vacuum forming process. The physical dental aligner is subsequently softened by heating. A thermal applier such as a stylus is then pressed against the physical dental aligner. The thermal applier moves across the surface to etch off materials to the wrinkles at the desired locations. Alternatively, wrinkles can be cut over the surface of the aligner by a position-controlled cutter or a laser beam.

In still another embodiment, aligner components are fabricated by CNC based manufacturing as described above in accordance with a digital dental aligner model. The digital dental aligner model includes wrinkle features over the surfaces of the dental aligner. The aligner components are fabricated in accordance with the digital dental aligner model having the wrinkle features. The dental aligner components are subsequently assembled to produce the physical dental aligner.

The wrinkled aligner can be milled out of a plastic block in accordance with digital aligner model. The milled out portion can be a portion of a tooth or a group of teeth. The inner hollow portion of the partially milled plastic block is then filled up with a soft holding material under heating. The holding material is soft at elevated temperatures and is hardened at room temperature. The holding material forms a handle after it cools off to room temperature. The partially milled plastic block can be held from outside while it is milled by CNC based manufacturing. An aligner having wrinkled surfaces is produced after machining. The holding material is subsequently removed by heating. The holding material can be wax, silicon, Epoxy or other kind of removable glue.

In yet another embodiment, a special clamp can also be used to hold the partially milled aligner parts in place while the rest of the aligner is milled using the CNC machine. The aligner components are assembled to form an aligner having one or more wrinkled surface. The aligner components include physical features to permit the aligner components to be assembled into the physical dental aligner having at least one wrinkled surface. The CNC based manufacturing can include one or more of milling, stereo lithography, laser machining, molding, and casting.

Figure 11:
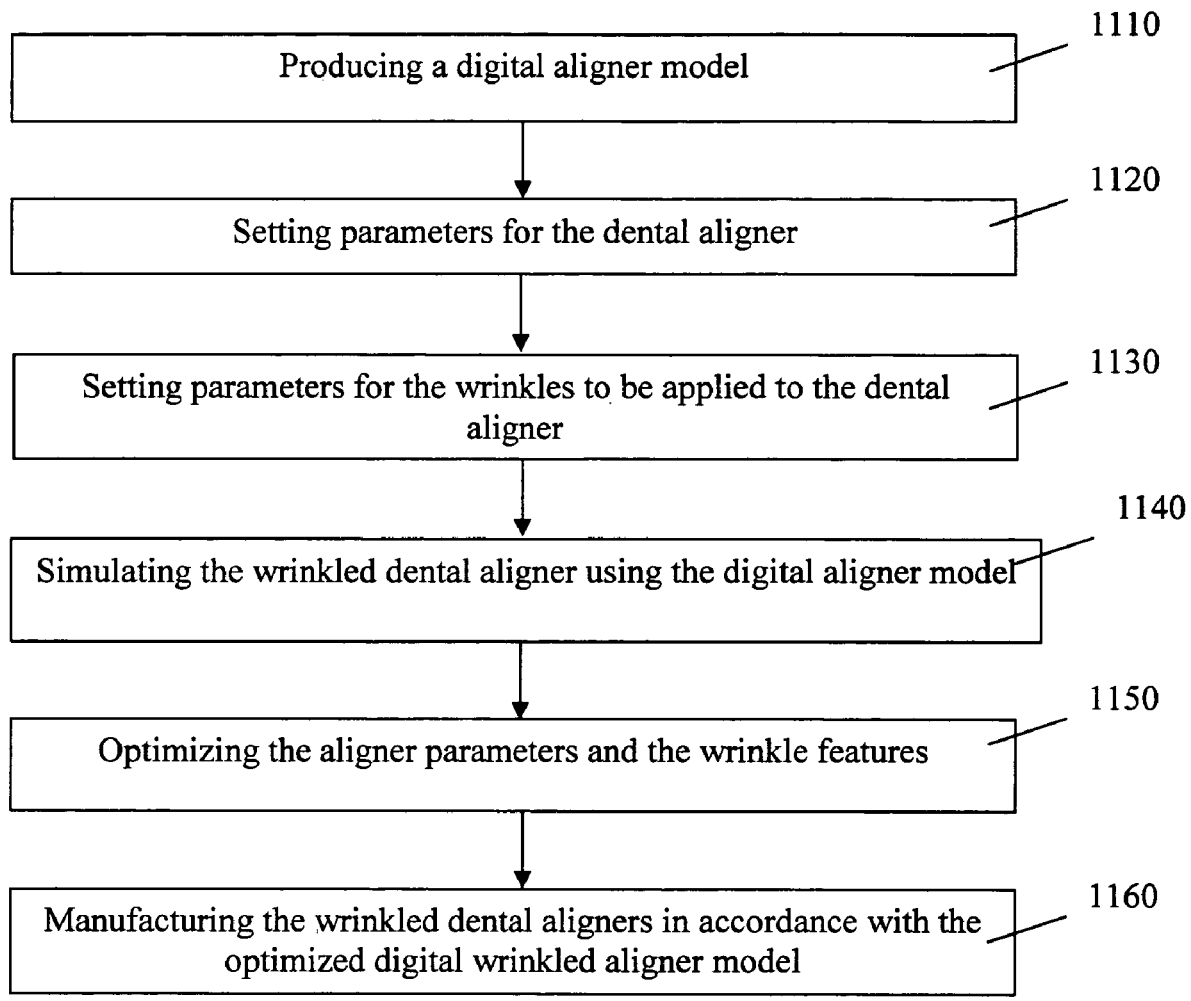
FIG. 11 illustrates the process of designing and fabrication of the wrinkled dental aligners.

FIG. 11 illustrates the process of designing and fabrication of the wrinkled dental aligners. A dental aligner model is first obtained using CAD software (step 1110). In general, the features of the wrinkles can be co-optimized with the properties of the aligners including the aligner material, the geometric parameters (curvature, thickness of the aligner), and the intended degree of teeth movement the aligner is to generate. These parameters are set in step 1120. A predetermined set of wrinkle features is then added to the surface of the digital aligner model in step 1130. The feature can include the locations, the orientations, and the density of the wrinkles, the width and the depth of the wrinkles, as well as the embedded materials that are used to produce the wrinkles.

The properties of the aligner and the features of the wrinkles on the aligners are next simulated for the optimal orthodontic performance and pre-stored in the digital aligner model in step 1140. The responses of the wrinkled aligners to various conditions during the patient's use of the wrinkled aligner are simulated using Finite Element Analysis (FEA). The conditions can include stresses applied by the patient during the biting, the wearing, and the removal of the aligner. The conditions can also include temperature changes when the patient has hot drinks or ice cream. Using Virtual Prototyping Software (a component of CAD software), the properties and performance of the wrinkled aligner can be analyzed under various simulated mechanical loads. The wrinkle features and the aligner properties can be varied in iterations for optimized performance in step 1150. Finally, the optimized wrinkle configurations are stored in a computer and used to control the fabrication of the wrinkled aligner in step 1160.

Although specific embodiments of the present invention have been illustrated in the accompanying drawings and described in the foregoing detailed description, it will be understood that the invention is not limited to the particular embodiments described herein, but is capable of numerous rearrangements, modifications, and substitutions without departing from the scope of the invention. The following claims are intended to encompass all such modifications.

What is claimed is:

1. A method for manufacturing a wrinkled dental aligner for a patient's tooth, comprising:
   developing a first digital dental aligner model comprising outer surfaces and inner surfaces designed to approximately follow at least some contours of outer surfaces of a digital dental arch model of the patient's dental arch in a target position, the first model configured to apply a system of forces to elicit movement of one or more teeth in accordance with a treatment plan;
   modifying the first model so as to create a second digital dental aligner model, the modifying comprising adding at least one predetermined wrinkle feature to the first digital dental aligner model, wherein the second model is configured to apply substantially the same system of forces to the teeth as the first model, and wherein the wrinkle feature is configured to reduce relaxation in a corresponding physical aligner after repeated use; and
   producing a physical dental aligner that is a physical embodiment of the second digital dental aligner model, the physical dental aligner having the wrinkle feature in accordance with said second digital dental aligner model, the physical dental aligner comprising a shell defining tooth receiving cavities, the wrinkle feature comprising a corrugated structure formed in a portion of material of the physical dental aligner that is in contact with the patient's tooth as the aligner is worn by the patient, the wrinkle feature configured to reduce loss of tooth movement eliciting forces due to relaxation in the physical aligner after repeated use, and wherein the wrinkle feature is other than contours of outer and inner surfaces of the aligner shell that approximately follow contours of the outer surfaces of the digital dental arch model of the patient's dental arch.

2. The method of claim 1, further comprising:
   producing the physical dental aligner having the wrinkle feature by vacuum forming over a dental arch model of the patient, wherein at least one surface of the dental arch model includes features to produce the wrinkle feature on the physical dental aligner.

3. The method of claim 1, further comprising:
   producing the wrinkle feature on the physical dental aligner by
   embedding a high-tension material under the surface of the physical dental aligner.

4. The method of claim 1, further comprising:
   producing the wrinkle feature on the physical dental aligner by cutting the surface of the physical dental aligner.

5. The method of claim 1, further comprising:
   producing the wrinkle feature on the physical dental aligner by etching the surface of the physical dental aligner by a thermal applier or a laser beam.

6. The method of claim 1, further comprising:
   fabricating a plurality of aligner components using CNC based manufacturing in accordance with the digital dental aligner model; and
   producing the physical dental aligner having the wrinkle feature by assembling the aligner components.

7. The method of claim 6, wherein the CNC based manufacturing includes one or more of milling, stereo lithography, laser machining, molding, and casting.

8. The method of claim 6, further comprising:
   producing physical features on the aligner components to permit the aligner components to be assembled into the physical dental aligner having at least one wrinkle feature.

9. The method of claim 1, further comprising:
  simulating the performance of the physical dental aligner under one or more stress conditions using the digital dental aligner model; and
  optimizing one or more parameters of the wrinkle feature based on the simulated behavior.

10. The method of claim 9, wherein optimizing one or more parameters of a wrinkle feature includes:
  determining one or more of the locations of the wrinkles;
  determining the orientations of the wrinkles;
  determining the spacing between adjacent wrinkles;
  determining the depths of the wrinkles; or
  any combination thereof.

11. The method of claim 10, wherein the wrinkle feature is oriented:
  horizontal to the base line of the dental aligner;
  vertical to the base line of the dental aligner; or
  any combination thereof.

12. The method of claim 10, wherein the wrinkle feature is oriented as a corrugated structure proximal to the base line of the dental aligner.

13. The method of claim 1, further comprising:
  developing the digital dental aligner model based on a digital dental arch model.

14. The method of claim 1, further comprising:
  segmenting the digital dental aligner model into a plurality of digital aligner components;
  producing physical aligner components using Computer Numerical Control (CNC) based manufacturing in accordance with the digital aligner components; and
  assembling the physical aligner components to form the wrinkled dental aligner.

15. A method for generating a wrinkled dental aligner for a patient's tooth, comprising:
  generating a first digital dental aligner model specifying at least one feature of the patient's tooth and configured to apply a system of forces to elicit movement of one or more teeth in accordance with a treatment plan, the first digital dental aligner model comprising outer surfaces and inner surfaces designed to approximately follow contours of outer surfaces of a digital model of the patient's dental arch in a target position; and
  modifying the first model so as to create a second digital dental aligner model, the modifying comprising adding at least one predetermined wrinkle feature to the first digital dental aligner model, the second model designed to apply substantially the same system of forces as the first model, and wherein the wrinkle feature comprises a corrugated structure formed proximal to a baseline and in a portion of material of the physical dental aligner that is in contact with the patient's tooth as the aligner is worn by the patient, and is selected to reduce loss of corrective force applied to the patient's teeth by a corresponding physical aligner after repeated use by the patient, wherein the wrinkle feature is other than contours of outer and inner surfaces of the aligner shell that approximately follow contours of the outer surfaces of the patients dental arch.

16. The method of claim 15, further comprising:
  determining one or more of the locations of the wrinkles;
  determining the orientations of the wrinkles,
  determining the spacing between adjacent wrinkles;
  determining the depths of the wrinkles; or
  any combination thereof.

17. The method of claim 16, wherein the wrinkle feature is designed to be oriented:
  horizontal to the base line of the dental aligner;
  vertical to the base line of the dental aligner; or
  any combination thereof.

18. The method of claim 16, wherein the wrinkle feature is designed to be oriented as a corrugated structure proximal to the base line of the dental aligner.

19. The method of claim 15, further comprising manufacturing the wrinkled dental aligner.

* * * * *